United States Patent
Marsh

(10) Patent No.: US 7,182,087 B1
(45) Date of Patent: Feb. 27, 2007

(54) DUAL POSITION HEARING PROTECTION DEVICE

(76) Inventor: Robert E. Marsh, 805 Westover Rd., Kansas City, MO (US) 64113

( * ) Notice: Subject to any disclaimer, the term of this patent is extended or adjusted under 35 U.S.C. 154(b) by 595 days.

(21) Appl. No.: 10/273,498

(22) Filed: Oct. 18, 2002

Related U.S. Application Data

(60) Provisional application No. 60/334,713, filed on Oct. 26, 2001.

(51) Int. Cl.
*A61F 11/06* (2006.01)

(52) U.S. Cl. .................. 128/867; 128/864; 181/135
(58) Field of Classification Search ............. 128/864, 128/865, 867; 381/328; 181/134, 135
See application file for complete search history.

(56) References Cited

U.S. PATENT DOCUMENTS

| | | | | |
|---|---|---|---|---|
| 3,415,246 A | * | 12/1968 | Hill | 128/864 |
| 5,002,151 A | * | 3/1991 | Oliveira et al. | 181/130 |
| 5,819,745 A | * | 10/1998 | Mobley et al. | 128/864 |
| 6,082,485 A | * | 7/2000 | Smith | 181/135 |
| 6,094,494 A | * | 7/2000 | Haroldson | 381/328 |
| 6,148,821 A | * | 11/2000 | Falco | 128/864 |

* cited by examiner

*Primary Examiner*—Vivian Chin
*Assistant Examiner*—Jason Kurr

(57) ABSTRACT

The present invention is a dual position hearing protection device. In one position, the device provides substantial sound attenuation and hearing protection. In the second position, an opening in the device permits sounds to enter the ear of the user relatively unobstructed. In the preferred embodiment of this invention the position of the device is changed simply by compressing the exposed end of the earplug.

14 Claims, 1 Drawing Sheet

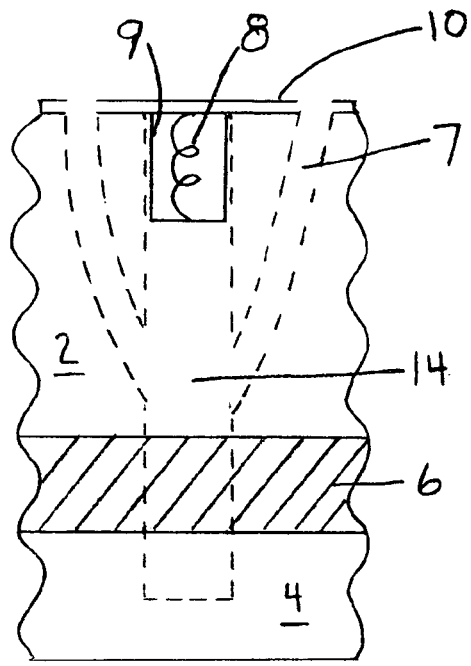
FIG 1
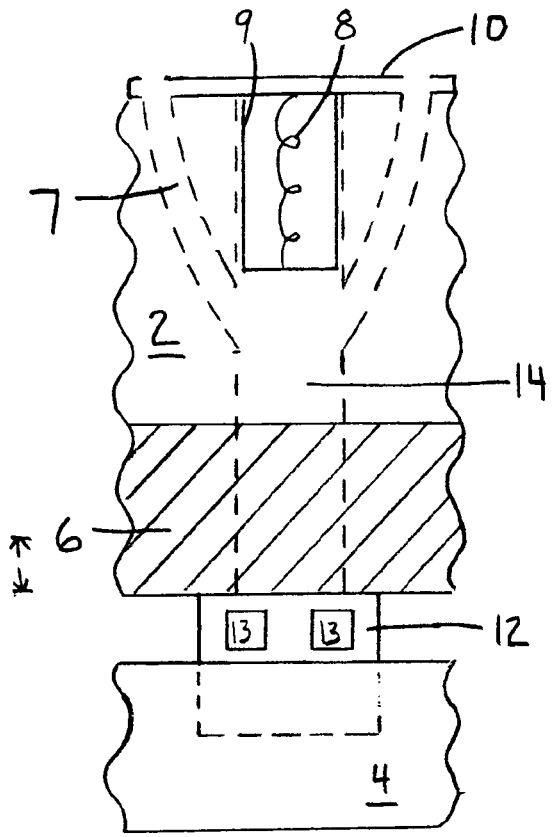
FIG 2
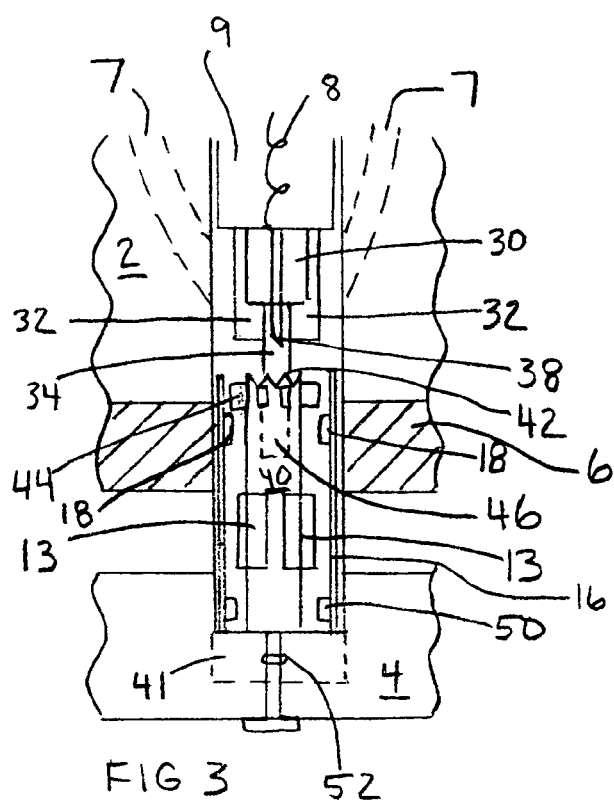
FIG 3
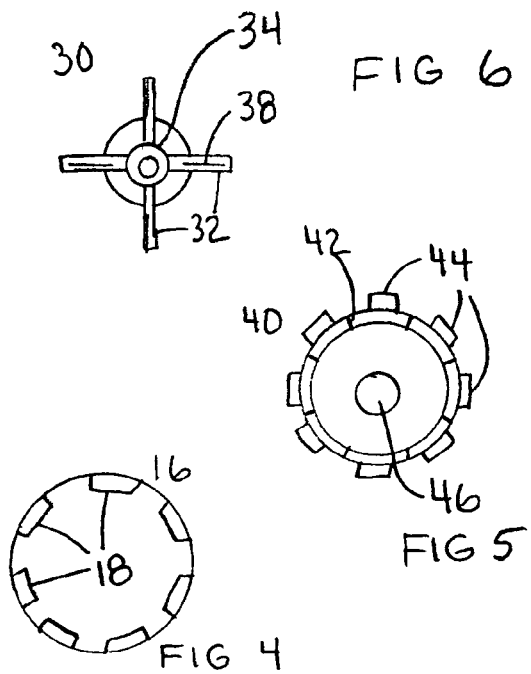
FIG 6
FIG 5
FIG 4

DUAL POSITION HEARING PROTECTION DEVICE

CROSS-REFERENCE TO RELATED APPLICATIONS

This application claims the benefit of U.S. Provisional Patent Application No. 60/334,713, filed Oct. 26, 2001.

STATEMENT REGARDING FEDERALLY SPONSORED RESEARCH OR DEVELOPMENT

Not Applicable.

BACKGROUND OF THE INVENTION

1. Field of the Invention

The present invention generally relates to devices for the protection of human hearing, and more particularly, to a hearing protection device that can be easily changed between a position which provides substantial hearing protection and a second position that permits more normal sound transmission.

2. Description of the Prior Art

Resilient foam ear plugs are widely used to provide hearing protection. These foam ear plugs are sometimes referred to as "self-adjustable." The generally tubular foam earplug is compressed and inserted into the ear canal, where it expands and conforms to the ear canal. In its expanded position, this foam earplug provides a high level of hearing protection. The "foam" used in these ear plugs can constitute one of many possible soft resilient materials, including silicone, neoprene, polyvinyl chloride, polyurethane, and others." These foam ear plugs are effective both as a result of the sound attenuation properties of the foam and the complete closure that results from expansion of the foam to contact the entire circumference of the ear canal. Thus it is important for the effectiveness of this ear plug that it remain firms positioned well within the ear canal in its expanded configuration.

Hearing protection is needed in situations such as firearm shooting activities in which there may be periods of loud noise followed by periods of no noise in which normal conversation is desirable. With prior art foam earplugs, however, conversation may be very difficult because of the high level of sound attenuation afforded by the ear plug. To permit more normal conversation the earplug must be removed, then re-compressed and reinserted into the ear canal before loud noises are again encountered. In addition, pressure differentials between the atmosphere and the inner ear resulting from the tight seal between the ear plug and the ear canal may be uncomfortable and may increase the user's desire to frequently remove the ear plug. Any situation in which a user's hands may become dirty (such as in handling a firearm or in an industrial workplace setting) the recompression of the earplug for reinsertion into the ear can result in contamination of the surface of the earplug and transfer of that contamination to the ear canal of the user.

Some hearing protection devices have attempted to selectively block certain sounds, such as the ear plug disclosed in U.S. Pat. No. 6,425,398, but with limited success. In many cases the effort to selectively block certain sounds results in less overall sound attenuation. No prior art hearing protection ear plug permits a user to physically switch the ear plug between a position in which substantial hearing protection is provided, to a position in which sound is only minimally obstructed and more normal conversation can take place.

SUMMARY OF THE INVENTION

The present invention is a dual position hearing protection device. In one position, the device provides substantial sound attenuation and hearing protection. In the second position, however, an opening in the device permits sounds to enter the ear to the user relatively unobstructed. In the preferred embodiment of this invention the position of the device is changed to simply by compressing the exposed end of the earplug.

It is an object of this invention to provide a hearing protection device that can be easily switched from a position of substantial hearing protection and sound attenuation to a position of reduced sound attenuation which permits more normal hearing and conversation. A further object of this invention to provide a hearing protection device that the user does not need to remove in order to carry on normal conversation. Still another object of the invention is to provide a compressible ear plug that conforms to the ear canal of the user but also permits convenient switching from a position providing substantial hearing protection and sound obstruction to a position of minimal sound obstruction. Still another object of the present invention is to permit switching between minimal and maximum sound attenuation positions while keeping the ear plug fully inserted in the ear canal.

BRIEF DESCRIPTION OF THE DRAWINGS

FIG. 1 shows a preferred embodiment of the hearing protection device in the closed position in which substantial hearing protection and sound attenuation is provided.

FIG. 2 shows a preferred embodiment of the hearing protection device in the open position in which sounds are minimally attenuated.

FIG. 3 shows the internal mechanism of a preferred embodiment of the hearing protection device that permits switching between open and closed positions by compression of the outer end of the earplug.

FIGS. 4, 5, and 6 show top views of different components of the internal mechanism of a preferred embodiment of the hearing protection device as discussed in more detail below.

DETAILED DESCRIPTION OF THE INVENTION

Referring to FIG. 1, a preferred embodiment of the hearing protection device is shown in the "closed" or substantial hearing protection and sound attenuation position. The ear plug includes a base plug 2 and a second plug 4. The base plug 2 includes at least a portion 6 that is resilient foam or a similar material. Ideally, the outer portions of ear plug components 2, 4, and 6, are all made of a resilient foam. The foam should be easily compressible by hand and should return to its original dimensions (or exert pressure against the ear canal of the user) when released. Suitable foams are well-known in the art. The internal structure of the earplug, described in more detail below, is located in the innerspace of base plug 2 as shown as 14 in FIG. 1. Alternatively, the internal structure could be located primarily within second plug 4. Ideally the diameter of the innerspace, 14 (and the internal components within that space as described below) are small relative to the overall diameter of the earplug and do not interfere with the compression, insertion and expansion of the ear plug.

Foam portion 6 of base plug 2 should be more substantially resilient since, as described in more detail below, this is a portion that must seal against second plug 4 in the closed position to insure substantial hearing protection and sound attenuation. As shown in FIG. 1, base plug 2 is first inserted into the ear of the user and second plug 4 and foam portion 6 would protrude outside of the ear canal of the user. In this embodiment the innerspace 14 is disposed within base plug 2 and foam portion 6. Sound channels 7 are located within base plug 2 and provide open space between innerspace 14 and the outside of the earplug. At the end of the innerspace closest to the ear drum of a user, compressible spring means 8 provides pressure to cause proper functioning of the internal mechanism described below. Spring means 8 could be made of a suitable foam that exerts suitable force as it attempts to return to its original dimensions, or it could be a spring or other structure exerting a suitable biasing force. In a preferred embodiment, the spring means 8 is a foam material that expands and contracts within a sleeve 9. Sleeve 9 is desirable because of the friction between spring means 8 and the foam of base plug 2. Sleeve 9 should be made of a suitable plastic or metal such that a small coefficient of friction exists between sleeve 9 and spring means 8. A cap, 10, is permanently attached to the top surface of base plug 2 (the surface nearest the ear drum of the user) to hold spring means 8 and sleeve 9 in position. It will be seen that an open passage exists through base plug 2 and foam portion 6, including passage through sound channels 7.

FIG. 2 shows the hearing protection device of the present invention in the "open" or relatively obstructed position. As shown in this figure, second plug 4 has been displaced such that a space exists between second plug 4 and foam portion 6. In this position sound enters in spaces 13 within the internal structure described in more detail below, passes through innerspace 14 and through sound channels 7 to reach the ear canal of the user. In this position spring means 8 has expanded from its compressed position in FIG. 1, thus providing a biasing force to displace second plug 4 into the open position. Foam portion 6 has also expanded to its largest possible dimensions, thus permitting the gap to exist between it and second plug 4.

FIG. 3 shows in more detail the inner mechanism of the present hearing protection device. In most general terms, this mechanism functions to change the location of second plug 4 and change the position of the present invention from the open to closed position, and vice versa. In this embodiment the position change occurs based on pressure applied against second plug 4 (pressing the earplug in the direction of the ear of the user thereby insuring that the ear plug remains in place in the ear). While the embodiment shown is a preferred one, other structures are possible to accomplish the same objectives and are well-known in the art. Some of the structure shown in FIG. 3 is also known in the art and has been used in such applications as ballpoint pens.

Returning to FIG. 3, portions of the hearing protection device described previously are again shown, including base plug 2, second plug 4, foam portion 6, spring means 8, sleeve 9, sound channels 7, and the spaces 13. The key components of the internal structure shown in FIG. 3 can be divided into primary three elements: (i) the switching sleeve shown in more detail in FIG. 4 and comprising elements 16 and 18, (ii) the switching ratchet shown in FIGS. 3 and 5 and comprising elements 13, 40, 42, 44, 46, and 50; and (iii) the switching actuator shown in FIG. 6 and comprising elements 30, 32, 34, and 38.

The switching sleeve shown in FIG. 4 is a cylinder, 16, rigidly attached to the inner surface of the innerspace 14 within base plug 2, and resting against (but not rigidly attached to) the inner surface of the innerspace within foam portion 6 and the innerspace 41 within second plug 4. Spaces 13 are disposed around the circumference of the switching sleeve cylinder, 16, and permit sounds to pass through the switching sleeve. Within the inner circumference of a cylinder 16, a series of tabs, 18, are spaced around that circumference and extend into the inside of the cylinder 16. As described in more detail below, whether tabs 18 rests against ratchet tabs, 44, determines the position of the device.

The switching ratchet shown in FIG. 5 is a rigid cylinder, 40, having a series of ratchet tabs, 44, disposed evenly around the outer circumference. Teeth, 42, that the top of the cylinder, 40, extend around the top of the cylinder, and as described below, engage actuator teeth 38 on the switching actuator. Cylinder 40 is rotatably attached to second plug 4 by pin 52, such that when cylinder 40 is held in the "closed" position as a result of a ratchet tabs 44 resting against tabs 18, second plug 4 is compressed against foam portion 6 and the device provides substantial hearing protection. Alternatively, when cylinder 40 is in the "open" position and has been displaced by the force of spring means 8 up to the pointed it has contacted stops 50 located at the end of the switching sleeve furthest from foam portion 6, space exists between foam portion 6 and second plug 4 permitting sounds to enter through spaces 13. Cylinder 40 is able to freely rotate, so that as the actuator teeth 38 on the switching actuator contact teeth 42 on the switching ratchet the cylinder 40 rotates (thus changing the alignment between tabs 18 and ratchet tabs 44).

FIG. 6 shows the switching actuator 30. The actuator is rigidly attached to spring means 8. Opposite spring means 8 is an actuator pin 34, that extends into the circular space 46 within cylinder 40. Evenly spaced around the circumference of the actuator 30 are 4 fins, 32, each of which have an actuator tooth, 38, as shown. Actuator tooth 38 engages the teeth 42 on the switching ratchet cylinder. In operation, when second plug 4 is depressed, teeth 42 engaged actuator teeth 38, causing the cylinder 40 of the switching ratchet to rotate. After one depression the cylinder rotates to that tabs 18 engage ratchet tabs 44 and hold the second plug 4 into the closed position. After another depression of second plug 4, the cylinder again rotates, but this time to a position that tabs 18 do not engage ratchet tabs 44 and the second plug 4 is extended to the full open position. The next depression again returns the second plug 4 to the closed position. Fins 32, tabs 18, and ratchet tabs 44 are all configured to cause the device to function in this manner.

In the open position, sound enters through spaces 13, passes through the open spaces between and around the various internal components in innerspace 14, and passes through sound channels 7 to enter the ear canal of the user. In the closed position, the compression of second plug 4 against foam portion 6 blocks most sound from reaching the innerspace of the ear plug and the ear canal of the user.

Other alternative structures are available to accomplish the objectives of this invention and afford the multiple position function of the present invention. Ideally any force applied to any portion of the ear plug should not tend to pull the ear plug out of the ear canal. As an alternative to the inward force required in the preferred embodiment disclosed above, rotation of the second plug to release the second plug (and/or lock it into the closed position) would be acceptable. In this alternative embodiment biasing means would still be desirable to move the second plug from the closed position to the open position without the need for external force applied to the ear plug that could pull the ear plug out of the ear canal of the user. Pressure against biasing means when moving the ear plug to the closed position is acceptable since it tends to force the ear plug into the ear canal of the user.

I claim:

1. An ear plug comprising:

A base plug having two ends;

said base plug having at least one open channel passing through the base plug;

a second plug; and switching means for moveably supporting said second plug in positions adjacent to one end of said base plug and permitting movement of said second plug between a first fixed position in contact with the adjacent end of said base plug and blocking said open channel through said base plug and a second fixed position not in contact with said adjacent end of said base plug.

2. The ear plug of claim 1 wherein said open channel in said base plug is open at each of said ends of said base plug.

3. The ear plug of claim 1 wherein said base plug is comprised of resilient foam.

4. The ear plug of claim 1 wherein said base plug is substantially cylindrical.

5. The ear plug of claim 3 wherein said second plug is comprised of resilient foam.

6. The ear plug of claim 5 wherein said base plug and second plug are substantially cylindrical.

7. The ear plug of claim 1 further comprising biasing means between said base plug and said second plug tending to force said second plug to said second position not in contact with said adjacent end of said base plug.

8. The ear plug of claim 7 wherein said open channel in said base plug is open at each of said ends of said base plug.

9. The ear plug of claim 7 wherein said base plug is comprised of resilient foam.

10. The ear plug of claim 7 wherein said base plug is substantially cylindrical.

11. The ear plug of claim 9 wherein said second plug is comprised of resilient foam.

12. The ear plug of claim 11 wherein said base plug and second plug are substantially cylindrical.

13. The ear plug of claim 7 wherein said biasing means is disposed primarily within said base plug.

14. The ear plug of claim 7 wherein said biasing means is disposed primarily within said second plug.

* * * * *